(12) United States Patent
Honkala et al.

(10) Patent No.: US 11,182,895 B2
(45) Date of Patent: Nov. 23, 2021

(54) APPARATUS AND ASSOCIATED METHOD FOR IMAGING

(71) Applicant: Nokia Technologies Oy, Espoo (FI)

(72) Inventors: Mikko Honkala, Espoo (FI); Akos Vetek, Espoo (FI); Tapio Taipalus, Espoo (FI); Harri Lindholm, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/468,964

(22) PCT Filed: Nov. 23, 2017

(86) PCT No.: PCT/FI2017/050813
§ 371 (c)(1),
(2) Date: Jun. 12, 2019

(87) PCT Pub. No.: WO2018/115570
PCT Pub. Date: Jun. 28, 2018

(65) Prior Publication Data
US 2019/0340754 A1 Nov. 7, 2019

(30) Foreign Application Priority Data

Dec. 22, 2016 (EP) ..................................... 16206200

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/7221* (2013.01); *A61B 5/7264* (2013.01);
(Continued)

(58) Field of Classification Search
CPC .... A61B 5/7221; A61B 5/7264; G06T 11/003
See application file for complete search history.

(56) References Cited

U.S. PATENT DOCUMENTS

2004/0022348 A1* 2/2004 Heumann ............ G01N 23/046
378/4
2009/0278928 A1* 11/2009 McCloskey ............. G06T 5/003
348/143

(Continued)

OTHER PUBLICATIONS

Examination Report for European Patent Application No. 16206200.4 dated Feb. 13, 2020, 4 pages.

(Continued)

*Primary Examiner* — Edward Park
(74) *Attorney, Agent, or Firm* — Locke Lord LLP

(57) ABSTRACT

An apparatus configured to generate an output quality error estimate using a machine-learning error estimation model to compare an output meeting a predetermined quality threshold with an output image reconstructed from a plurality of images, and provide the output quality error estimate for use in estimating if a second subsequent image is required, in addition to a first subsequent image to obtain a cumulative output having an output quality error meeting a predetermined error threshold. Also an apparatus configured, using a received output quality error estimate generated using a machine-learning error estimation model as above, to estimate if a second subsequent image is required, in addition to a first subsequent image, to obtain a cumulative output having an output quality error meeting a predetermined error threshold.

16 Claims, 7 Drawing Sheets

(51) Int. Cl.
  *G06T 11/00* (2006.01)
  *A61B 5/245* (2021.01)
(52) U.S. Cl.
  CPC .............. *G06T 11/003* (2013.01); *A61B 5/245* (2021.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/30004* (2013.01)

(56) References Cited

U.S. PATENT DOCUMENTS

| | | | |
|---|---|---|---|
| 2012/0177274 A1* | 7/2012 | Koehler | G06T 11/008 382/131 |
| 2015/0196265 A1 | 7/2015 | Suzuki | |
| 2015/0201895 A1 | 7/2015 | Suzuki | |
| 2016/0093022 A1* | 3/2016 | Lee | G06T 3/4053 382/300 |
| 2019/0340754 A1* | 11/2019 | Honkala | A61B 6/5211 |

OTHER PUBLICATIONS

International Search Report for International Patent Application No. PCT/FI2017/050813 dated Jan. 12, 2018, 3 pages.

Written Opinion of the International Searching Authority for International Patent Application No. PCT/FI2017/050813 dated Jan. 12, 2018, 7 pages.

\* cited by examiner

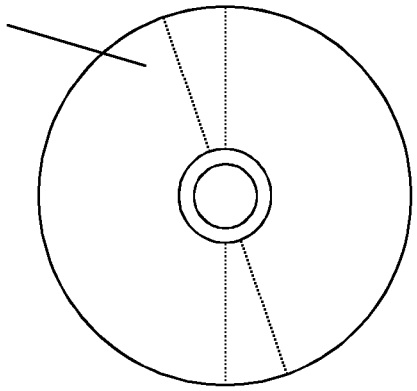

Figure 11

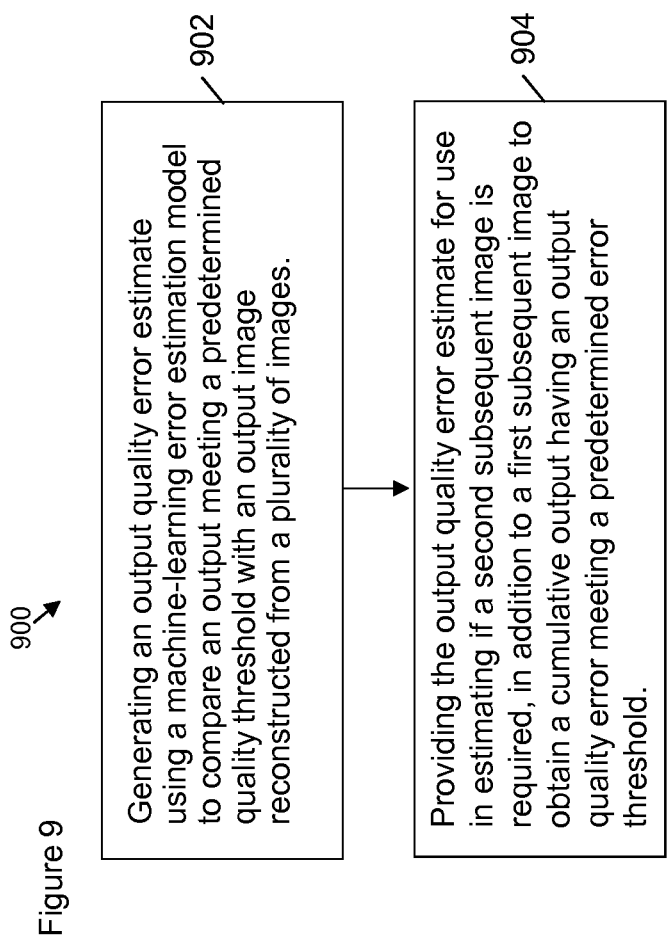

Figure 9

900 — Generating an output quality error estimate using a machine-learning error estimation model to compare an output meeting a predetermined quality threshold with an output image reconstructed from a plurality of images. — 902

Providing the output quality error estimate for use in estimating if a second subsequent image is required, in addition to a first subsequent image to obtain a cumulative output having an output quality error meeting a predetermined error threshold. — 904

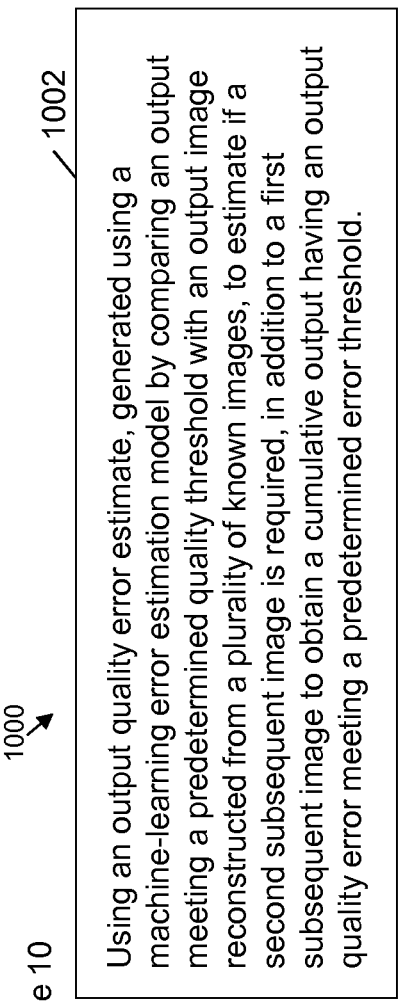

Figure 10

1000 — Using an output quality error estimate, generated using a machine-learning error estimation model by comparing an output image meeting a predetermined quality threshold with an output image reconstructed from a plurality of known images, to estimate if a second subsequent image is required, in addition to a first subsequent image to obtain a cumulative output having an output quality error meeting a predetermined error threshold. — 1002

APPARATUS AND ASSOCIATED METHOD FOR IMAGING

TECHNICAL FIELD

The present disclosure relates to imaging apparatus, associated methods and computer program code, for example computer tomography (CT) and X-ray imaging. Certain examples relate to apparatus configured to use a machine-learning error estimation model to generate an output quality error estimate and/or use an output quality error estimate to determine whether further images are required to obtain a required reconstructed image quality.

BACKGROUND

Research is currently being done to improve imaging apparatus and methods, in particular in relation to radiological imaging such as X-ray and CT imaging.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising at least one processor; and at least one memory including computer program code, the at least one memory and the computer program code configured to, with the at least one processor, cause the apparatus to:
  generate an output quality error estimate using a machine-learning error estimation model to compare an output meeting a predetermined quality threshold with an output image reconstructed from a plurality of images, and
  provide the output quality error estimate for use in estimating if a second subsequent image is required, in addition to a first subsequent image to obtain a cumulative output having an output quality error meeting a predetermined error threshold.

According to a further aspect, there is provided an apparatus comprising: at least one processor; and at least one memory including computer program code, the at least one memory and the computer program code configured to, with the at least one processor, cause the apparatus to:
  using a received output quality error estimate, generated using a machine-learning error estimation model by comparing an output meeting a predetermined quality threshold with an output image reconstructed from a plurality of images to estimate if a second subsequent image is required, in addition to a first subsequent image to obtain a cumulative output having an output quality error meeting a predetermined error threshold.

The output image used to generate the output quality error estimate may be reconstructed from a plurality of images recorded using particular imaging parameters, and the first and second subsequent images may be recorded using the particular imaging parameters. In this way the data used to train the machine-learning error estimation model corresponds to the subsequent recorded images.

The output quality error estimate may be one or more of:
a reconstruction error indicating a difference between:
  an image reconstructed from a plurality of standard power classed images, the image meeting the predetermined quality threshold; and
  an image reconstructed from a plurality of low power classed images;
a diagnostic error indicating a difference between:
  a diagnosis meeting the predetermined quality threshold; and
  a diagnosis determined from an image reconstructed from a plurality of low power classed images; and
a segmentation error indicating a difference between:
  an indication of material type meeting the predetermined quality threshold obtained from an image reconstructed from a plurality of standard power classed images; and
  an indication of material type determined from an image reconstructed from a plurality of low power classed images.

The predetermined error threshold may be one of:
an acceptable image noise threshold, and the output quality error of the cumulative output indicates that image noise of the cumulative output image meets or is below the predetermined acceptable image noise threshold;
a diagnosis confidence threshold, and the output quality error of the cumulative output indicates a confidence level that a diagnosis obtained from the cumulative output exceeds the predetermined diagnosis confidence threshold; and
a segmentation confidence threshold, and the output quality error of the cumulative output indicates a confidence level that a segmentation obtained from the cumulative output exceeds the predetermined segmentation confidence threshold.

The apparatus may be configured to:
if the output quality error of the cumulative output meets or is below the predetermined error threshold, provide an indication to stop recording images; and
if the output quality error exceeds the predetermined error threshold, provide an indication to record the second subsequent image.

The apparatus may be configured to, if the output quality error of the cumulative output exceeds the predetermined error threshold, obtain an updated output quality error for the cumulative output including the second subsequent image.

The first subsequent image may be taken at a particular angular projection with respect to the subject, and the second subsequent image may be taken at a different particular angular projection with respect to the subject than the first subsequent image. The first and second subsequent images may be taken at the same particular angular projection with respect to the subject.

The apparatus may be configured to estimate, in a time which is low enough to allow for the estimating to take place between successive subsequent images, if the second subsequent image is required. The time to estimate if a second subsequent image is required may be less than 1 second, less than 0.5 seconds, less than 0.2 seconds, or less than 100 ms.

The apparatus may be configured to:
obtain a plurality of subsequent images including the first and second subsequent images; and
after estimating that no further subsequent images are required to obtain a cumulative output having an output quality error meeting a predetermined error threshold, obtain the cumulative output by reconstructing an output image from the plurality of subsequent scans.

The apparatus may be configured to:
estimate that a cumulative output having an output quality error meeting a predetermined error threshold cannot be obtained by recording a second and further subsequent images; and
provide an indication to stop recording images.

The first and second subsequent images may be X-ray images, Computer Tomography (CT) scan images, Magnetic Resonance Imaging (MRI) images, functional Magnetic Resonance Imaging (fMRI) images, fusion imaging (a combination of Computer Tomography (CT) imaging and Positron Emission Tomography (PET) imaging), positron emission tomography (PET) images, single photon emission tomography (SPET) images, Magnetoencephalography (MEG) images or ultrasound images.

The apparatus may be configured to estimate if a second subsequent image is required following one or more of: a single first subsequent image, and a plurality of first subsequent images.

According to a further aspect, there is provided a computer-implemented method comprising:
generating an output quality error estimate using a machine-learning error estimation model to compare an output meeting a predetermined quality threshold with an output image reconstructed from a plurality of images, and
providing the output quality error estimate for use in estimating if a second subsequent image is required, in addition to a first subsequent image to obtain a cumulative output having an output quality error meeting a predetermined error threshold.

According to a further aspect, there is provided a computer-implemented method comprising:
using an output quality error estimate, generated using a machine-learning error estimation model by comparing an output meeting a predetermined quality threshold with an output image reconstructed from a plurality of images, to estimate if a second subsequent image is required, in addition to a first subsequent image to obtain a cumulative output having an output quality error meeting a predetermined error threshold.

The steps of any method disclosed herein do not have to be performed in the exact order disclosed, unless explicitly stated or understood by the skilled person.

Corresponding computer programs for implementing one or more steps of the methods disclosed herein are also within the present disclosure and are encompassed by one or more of the described examples.

Thus according to a further aspect, there is provided a computer-program comprising code configured to:
generate an output quality error estimate using a machine-learning error estimation model to compare an output meeting a predetermined quality threshold with an output image reconstructed from a plurality of images, and
provide the output quality error estimate for use in estimating if a second subsequent image is required, in addition to a first subsequent image to obtain a cumulative output having an output quality error meeting a predetermined error threshold.

Also, according to a further aspect, there is provided a computer-program comprising code configured to: using an output quality error estimate, generated using a machine-learning error estimation model by comparing an output meeting a predetermined quality threshold with an output image reconstructed from a plurality of images, estimate if a second subsequent image is required, in addition to a first subsequent image to obtain a cumulative output having an output quality error meeting a predetermined error threshold.

One or more of the computer programs may, when run on a computer, cause the computer to configure any apparatus, including a battery, circuit, controller, or device disclosed herein or perform any method disclosed herein. One or more of the computer programs may be software implementations, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

One or more of the computer programs may be provided on a computer readable medium, which may be a physical computer readable medium such as a disc or a memory device, may be a non-transient medium, or may be embodied as a transient signal. Such a transient signal may be a network download, including an internet download.

The present disclosure includes one or more corresponding aspects, examples or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:

FIG. 9 shows the main steps of a method of using the present apparatus; and

FIG. 10 shows the main steps of a method of using the present apparatus;

FIG. 11 shows a computer-readable medium comprising a computer program configured to perform, control or enable the methods of FIGS. 9 and/or 10.

DESCRIPTION OF SPECIFIC EXAMPLES

In medical X-ray imaging (including CT imaging) it is desirable to reduce/minimize the radiation dose received by the patient. Unnecessary dosage of radiation due to receiving a CT scan or X-ray imaging is harmful for humans and animals. There are growing concerns on radiation-induced genetic, cancerous and other diseases. Also, in non-medical applications, in some cases it may be beneficial to reduce the radiation dose used to investigate, for example, a radiation-sensitive biological or chemical sample of material to obtain information about the sample before it breaks down. Certain examples described herein may provide a technical effect of reducing the radiation dose provided to a subject being scanned.

Figure 1:
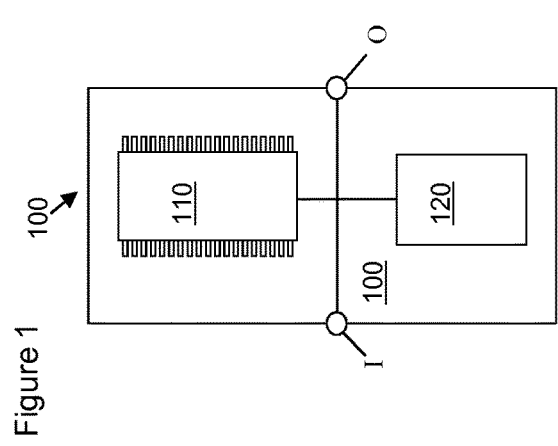
FIG. 1 shows an example apparatus according to the present disclosure.

FIG. 1 shows an apparatus 100 comprising a processor 110, memory 120, input I and output O. In this example only one processor and one memory are shown but it will be appreciated that other examples may utilise more than one processor and/or more than one memory (e.g. same or different processor/memory types). The apparatus 100 may be or may comprise an application specific integrated circuit (ASIC). The apparatus 100 may be or may comprise a field-programmable gate array (FPGA). The apparatus 100 may be a module for a device, or may be the device itself, wherein the processor 110 is a general purpose CPU and the memory 120 is general purpose memory.

The input I allows for receipt of signalling to the apparatus 100 from further components. The output O allows for onward provision of signalling from the apparatus 100 to further components. In this example the input I and output O are part of a connection bus that allows for connection of the apparatus 100 to further components. The processor 110 is a general purpose processor dedicated to executing/processing information received via the input I in accordance with instructions stored in the form of computer program code on the memory 120. The output signalling generated by such operations from the processor 110 is provided onwards to further components via the output O.

The memory 120 (not necessarily a single memory unit) is a computer readable medium (such as solid state memory, a hard drive, ROM, RAM, Flash or other memory) that stores computer program code. This computer program code stores instructions that are executable by the processor 110, when the program code is run on the processor 110. The internal connections between the memory 120 and the processor 110 can be understood to provide active coupling between the processor 110 and the memory 120 to allow the processor 110 to access the computer program code stored on the memory 120.

In this example the input I, output O, processor 110 and memory 120 are electrically connected internally to allow for communication between the respective components I, O, 110, 120, which may be located proximate to one another as an ASIC. In this way the components I, O, 110, 120 may be integrated in a single chip/circuit for installation in an electronic device. In other examples, one or more or all of the components may be located separately (for example, throughout a portable electronic device such as devices 200, 300, or within a network such as a "cloud" and/or may provide/support other functionality).

Figure 2:
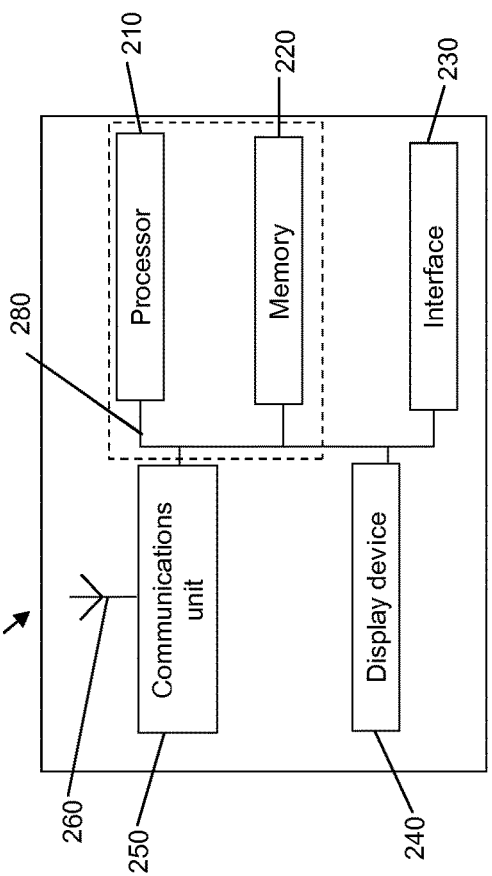
FIG. 2 illustrates another example apparatus according to the present disclosure.

One or more examples of the apparatus 100 can be used as a component for another apparatus as in FIG. 2, which shows a variation of apparatus 100 incorporating the functionality of apparatus 100 over separate components. In other examples the device 200 may comprise apparatus 100 as a module (shown by the optional dashed line box) for a mobile phone or PDA or audio/video player or the like. Such a module, apparatus or device may just comprise a suitably configured memory and processor.

The example apparatus/device 200 comprises a display 240 such as, a Liquid Crystal Display (LCD), e-Ink, or touch-screen user interface (like a tablet PC). The device 200 is configured such that it may receive, include, and/or otherwise access data. For example, device 200 comprises a communications unit 250 (such as a receiver, transmitter, and/or transceiver), in communication with an antenna 260 for connection to a wireless network and/or a port (not shown). Device 200 comprises a memory 220 for storing data, which may be received via antenna 260 or user interface 230. The processor 210 may receive data from the user interface 230, from the memory 220, or from the communication unit 250. Data may be output to a user of device 200 via the display device 240, and/or any other output devices provided with apparatus. The processor 210 may also store the data for later user in the memory 220. The device contains components connected via communications bus 280.

The communications unit 250 can be, for example, a receiver, transmitter, and/or transceiver, that is in communication with an antenna 260 for connecting to a wireless network and/or a port (not shown) for accepting a physical connection to a network, such that data may be received via one or more types of network. The communications (or data) bus 280 may provide active coupling between the processor 210 and the memory (or storage medium) 220 to allow the processor 210 to access the computer program code stored on the memory 220.

The memory 220 comprises computer program code in the same way as the memory 120 of apparatus 100, but may also comprise other data. The processor 210 may receive data from the user interface 230, from the memory 220, or from the communication unit 250. Regardless of the origin of the data, these data may be outputted to a user of device 200 via the display device 240, and/or any other output devices provided with apparatus. The processor 210 may also store the data for later user in the memory 220.

Figure 3:
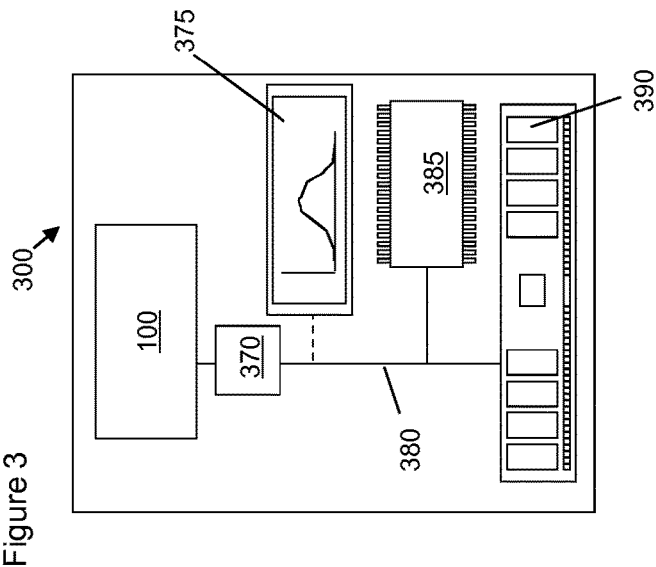
FIG. 3 illustrates a further example apparatus according to the present disclosure.

Device/apparatus 300 shown in FIG. 3 may be an electronic device (including a tablet personal computer), a portable electronic device, a portable telecommunications device, or a module for such a device. The apparatus 100 can be provided as a module for device 300, or even as a processor/memory for the device 300 or a processor/memory for a module for such a device 300. The device 300 comprises a processor 385 and a storage medium 390, which are electrically connected by a data bus 380. This data bus 380 can provide an active coupling between the processor 385 and the storage medium 390 to allow the processor 380 to access the computer program code.

The apparatus 100 in FIG. 3 is electrically connected to an input/output interface 370 that receives the output from the apparatus 100 and transmits this to the device 300 via data bus 380. Interface 370 can be connected via the data bus 380 to a display 375 (touch-sensitive or otherwise) that provides information from the apparatus 100 to a user. Display 375 can be part of the device 300 or can be separate. The device 300 also comprises a processor 385 that is configured for general control of the apparatus 100 as well as the device 300 by providing signalling to, and receiving signalling from, other device components to manage their operation.

The storage medium 390 is configured to store computer code configured to perform, control or enable the operation of the apparatus 100. The storage medium 390 may be configured to store settings for the other device components. The processor 385 may access the storage medium 390 to retrieve the component settings in order to manage the operation of the other device components. The storage medium 390 may be a temporary storage medium such as a volatile random access memory. The storage medium 390 may also be a permanent storage medium such as a hard disk drive, a flash memory, or a non-volatile random access memory. The storage medium 390 could be composed of different combinations of the same or different memory types.

Examples described herein relate to a machine-learning model which is pre-trained using previously-obtained data, to compare a final result from the previously obtained data (i.e. a complete reconstructed image from several full power scans, or a ground truth diagnosis) with a reconstructed scan obtained from previously obtained scans of the same type as scans to be taken, such as a series of low power scans. In some examples, the scans to be taken may be recorded using the same particular imaging parameters, such as same angular projection, power, and exposure time, as the previously-obtained data. A machine learning model can determine a function f such that Y=f(X). In machine-learning, the term "ground truth" refers to data samples, containing well known and correct pairs of X and Y, which are used to train a model and to validate the generalization performance of such a model.

An example of a "low dose" of radiation from a low power scan is between approximately 1-3 mSv (but this may vary depending on the target being imaged) compared with above approximately 3 mSv for a standard dose. Low dose X-ray scanning may use multiple low dose scans of the same subject, and an image may be reconstructed from the multiple low-dose scans. The multiple scans may be recorded from the same position (thus recording a plurality of repeat scans), or may be taken from different positions with respect to the subject, such as at different angular projections (for example by rotating the subject, or the imaging apparatus, between scans).

The machine-learning model therefore "learns" (is provided with data which indicates) how a low-power scan from a series of low-power scans compares with a full "ideal" output (a full 3D reconstructed image or a complete diagnosis, for example). From this knowledge, the machine-learning model can make a prediction whether a subsequent low-power scan is likely to provide enough information (along with any other low-power scans taken in the scanning session) to allow a good enough reconstruction or diagnosis to be eventually obtained.

Examples described herein include an apparatus configured to generate an output quality error estimate by using a machine-learning error estimation model to compare an output meeting a predetermined quality threshold with an output image reconstructed from a plurality of images, and provide the output quality error estimate for use in estimating if a second subsequent image is required, in addition to a first subsequent image to obtain a cumulative output having an output quality error meeting a predetermined error threshold. Such an apparatus may be considered to be used in a "training" stage, of training the machine-learning error estimation model for subsequent use.

The machine-learning error estimation model is provided with already-captured images/information of two types. A first type of information represents an "ideal" or best case, and may be called an output meeting a predetermined quality threshold (that is, the output is of a high enough quality that it may be used as required, for example to obtain a diagnosis from, or it is of sufficient resolution that particular features can be identified in the image). Examples include a fully reconstructed image obtained from a large number of standard power X-ray scans, or a "ground truth" diagnosis. A second type of information represents the type of data which is going to be obtained in a subsequent imaging/scanning procedure, and may be termed an output image reconstructed from a plurality of images. Examples include an image reconstructed from plurality of low power X-ray scans (there may be fewer such low power X-ray scans than standard power X-ray scans used to obtain the "ideal" case), and a predicted diagnosis obtained from a plurality of low power scans.

The second type of information may be recorded using the same particular imaging parameters which are also used to capture information in subsequent scans in some examples. The machine-learning error estimation model can analyse the subsequently recorded scans, in-between scans, to determine if those subsequent scans are sufficient to obtain a required reconstructed output with the required quality, by determining if those scans would have an output quality error meeting a predetermined error threshold, which indicates a difference between the expected reconstructed output and an ideal case. The apparatus may determine that a further scan is required to reduce the output quality error and try to meet the predetermined error threshold. The apparatus may determine that even if a further scan is obtained, the quality of the reconstructed output from the subsequent scans will still not be of a high enough quality/still not meet the predetermined error threshold.

Examples described herein include an apparatus configured to, using a received output quality error estimate, generated using a machine-learning error estimation model by comparing an output meeting a predetermined quality threshold with an output image reconstructed from a plurality of images, estimate if a second subsequent image is required, in addition to a first subsequent image to obtain a cumulative output having an output quality error meeting a predetermined error threshold. Such an apparatus may be considered to be used in a "scanning" or "inference" stage, of subsequently using the trained machine-learning error estimation model during scanning a subject.

Examples described herein may allow for estimation of the quality of the reconstructed image online ("on-the-fly") in a very fast manner, e.g. fast enough to take place between successive scans. This is in contrast to de-noising methods which run offline after all the scans have been recorded. De-noising can also be referred to a reconstructing. Deep learning and convolutional de-noising algorithms (amongst other iterative reconstruction algorithms) for X-rays and CT scans can be used to de-noise X-ray images. However, such algorithms are used after all scans have been recorded, and not to decide dynamically (between scans) whether the scanning should continue or not. This is because these algorithms can take a long time to run, much longer than can practically be spent between taking scans of the same subject. Reconstructing an output all scans have been taken requires the scanning power, and thus the resulting dosage, to be predefined, because a determination of final reconstructed image quality cannot be obtained during scanning. If the power is too low, this may result in poor reconstruction quality, and thus the scanning process needs to start again afresh with a higher power (which may not always be possible depending on determined safe expose levels).

The fast runtime of examples disclosed herein is achieved by training the machine-learning model offline using a large number of sample images, before commencing scanning the present subject. Thus this overall method may allow for much lower radiation doses to be required than a maximum determined safe dose, due to the dynamic assessment, between successive scans, of the estimated quality of the final reconstruction.

As an example, a safe number of scans taken may be determined to be 50 before exceeding the recommended radiation exposure due to scanning, but it may be that a good enough image may be reconstructed from only 10 such scans. In this example the subsequent 40 scans would not be required, and by not recording the extra 40 scans, the exposure of the subject to radiation is reduced compared with recording all 50 scans.

The amount of radiation dose per scan and the speed of successive scans are parameters that can be estimated separately either offline (prior to taking scans) or online (during and/or between taking scans). These parameters depend, for example, on the maximum dose, minimum quality, and the speed of the process of determining the output quality error. In some examples the process of determining the output quality error and determining whether or not this meets the predetermined error threshold (which may be performed by a "reconstruction quality estimation algorithm", which estimates the quality of a reconstruction which would be obtained from the subsequent scans.

There may be a decision point e.g. after each scan, or less often (e.g. after each group of 3, 5 or 10 scans), at which it is decided whether another scan or set of scans should be recorded. Thus, the apparatus may be configured to estimate if a second subsequent image is required following a single first subsequent image (e.g. after each subsequent scan), and/or a plurality of first subsequent images (e.g. after a group of two or more subsequent scans). For example, the apparatus may make the estimation as a function of how different the output quality error of the cumulative output is compared with the output quality error estimate determined by the machine learning model during training. For example, a larger difference in error may cause the apparatus to make the estimation after a group of a further five subsequent scans are recorded, whereas a small different in error may cause the apparatus to make the estimation after each subsequent scan. Other examples are possible.

The end result of this on-the-fly determination of the requirement for further scans may be that fewer images overall are taken compared with a number of required scans determined offline, or that more lower-power images may be taken, thereby reducing the overall dose administered compared with a dose determined offline.

Obtaining an indication of whether further scans are required or not (for radiation and non-radiation based scanning) may help to minimise or reduce the time the subject needs to remain stationary during scans. For example a claustrophobic person, or child, may be able to stay still in an MRI machine for five minutes but no longer. If it can be determined, by determining if the overall final reconstructed scan will be of good enough quality after five minutes of scanning, then this avoids the subject being required to stay still for the otherwise expected time for a series of scans to be taken of e.g. 15 minutes.

Prior to taking scans from the subject (the "subsequent" scans, since these scans are recorded subsequent to/following the scans used to train the machine learning error estimation model), the machine-learning model is trained to "learn" about the type of scans which will be taken.

There are several ways of obtaining the data required to train the machine learning model. The machine-learning model may be trained, for example, using data (e.g. images, diagnoses) already taken from multiple previous subjects. If the subject to be scanned is, for example, a human abdomen, then multiple previous scans of human abdomens may be used to train the machine-learning model. If the subject is suspected of having a particular medical condition, then multiple previous scans of subjects with the same particular medical condition may be used to train the machine-learning model.

There also exists a large number of full power scans available from previous imaging. The noise that ultra-low-power scanning typically creates may be simulated in these scans, and the simulated ultra-low-power scans, together with the corresponding full power scans, may be used to train the machine learning error estimation model, so the model can be used to estimate the reconstructed scan quality from subsequently recorded ultra-low-power scans. Large amounts of both ultra-low-power and full power scans may be collected from phantoms (an object designed to be imaged which will respond in a similar manner to how human tissues and organs would act in that specific imaging modality), cadavers or animals (dead or alive), and this data may be used to train the machine learning model.

Once the data for training purposes has been collected, two machine-learning models may be built. Firstly, a quality assessment model, may be built, which assesses the quality of the de-noising (that is, estimates whether a reconstruction from the acquired scans will meet the predetermined error threshold, indicating that it is of sufficient quality). The quality assessment model is such that at the inference phase (during the scanning process) it can be run very quickly, so it is possible to make a dynamic quality assessment of data collected during the scanning process (in-between scans). The quality assessment model may be called an error estimation model, or a machine learning error estimation model, because it may be used to estimate an error between the expected reconstructed output from the scan or scans recorded for a particular subject/scanning procedure, and an "ideal" reconstruction obtained from optimal data e.g. standard power data or a large number of scans, which meets a predetermined quality threshold, indicating it is good enough.

Secondly a reconstruction model is required, which creates a de-noised reconstruction from multiple recorded scans e.g. N consecutive scans of the same subject. The final reconstruction model is only run after all the scans have been taken, so it does not need to be as fast as the quality assessment model. Any suitable reconstruction method can be used. Any machine-learning (e.g. a denoising 2D or 3D convolutional neural network (CNN)) or inverse modelling method may be used to build these models (e.g. analytical, iterative or hybrid CT reconstruction methods).

It may also be possible to build a combined model. Some approximate reconstruction methods and may be fast enough to be run between scans. Such approximate reconstruction methods may require additional support/information to estimate the quality of a reconstruction. Therefore a combined method that uses a known approximate reconstruction method and also uses the machine learning quality estimation described herein may be used.

Many reconstruction methods exist (e.g. analytical, heuristic and machine-learning based). These can be used in examples disclosed herein as part of the quality assessment model, or as part of the final reconstruction model.

The machine-learning error estimation model has been trained, as described above, to obtain an output quality error estimate. This allows the machine-learning error estimation model to be able to correlate a scan recorded following/subsequent to the machine-learning model training with an output quality error which a reconstruction obtained using that scan would have. The subsequent scans in some examples may be recorded using the same particular imaging parameters as a corresponding scan used for training the machine-learning model, so that the machine-learning model can use the data is has been trained with regarding a scan of that type and "look up"/indicate an output quality error determined for that type of scan. The output quality error indicates how different the reconstruction would be using the subsequently recorded scan (and combination of that scan with any other subsequently recorded scans for the subject in the same imaging session, for example in a series of scans recorded at different angular projections) from an "ideal" case.

The scanning system may take successive multiple low-power CT scans or X-ray images. During scanning, the pre-trained machine-learning model can be used to decide whether to continue the scanning process by recording further subsequent scans, or terminate it. This decision flow is shown in FIG. 4.

Figure 4:
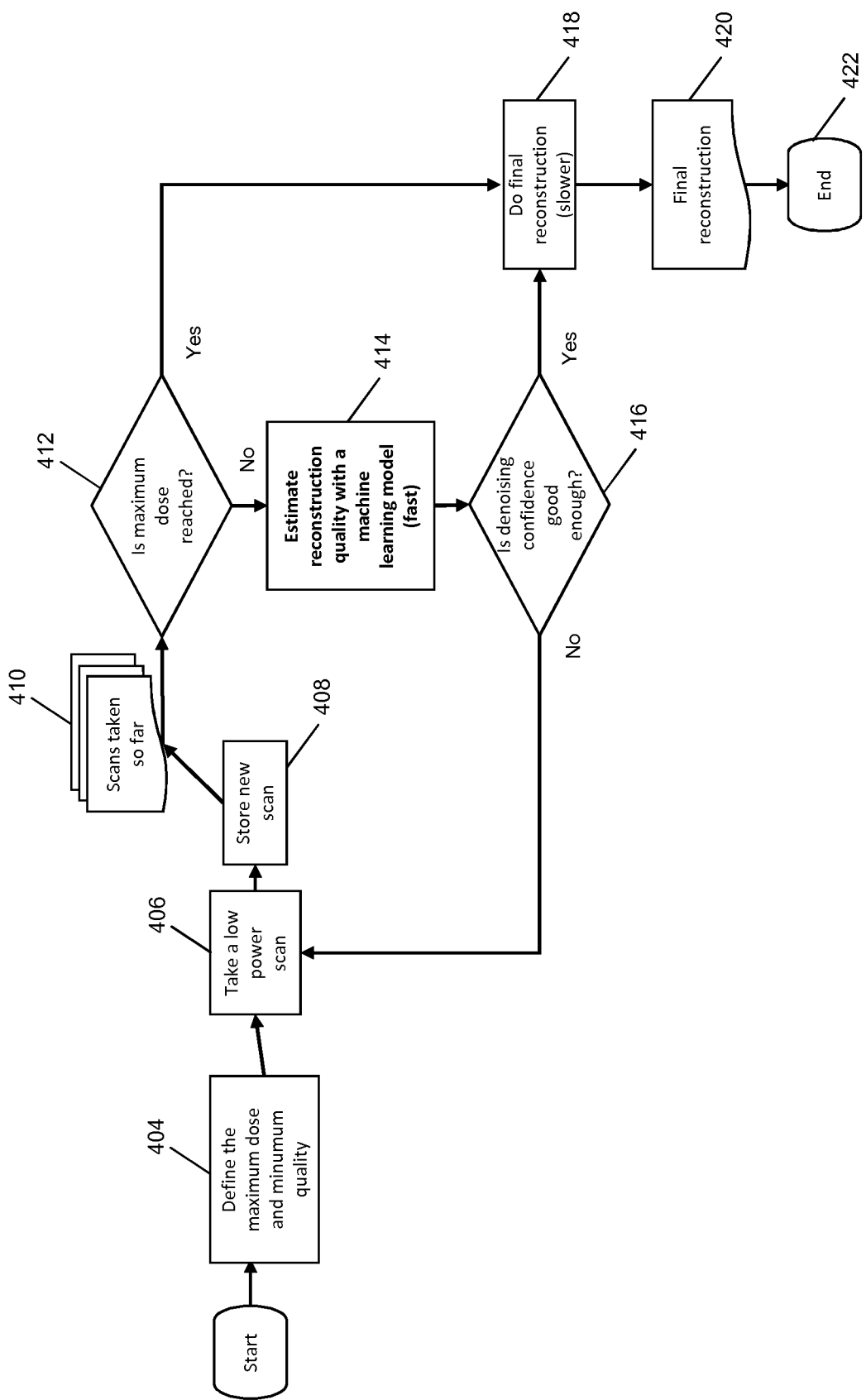
FIG. 4 illustrates an example scanning process using a machine-learning model.

FIG. 4 shows an example process flow for using apparatus as described herein for scanning a subject. The scans may be, for example, X-ray images, Computer Tomography scan images, or Magnetic Resonance Imaging images. One or more of the steps in FIG. 4 may be performed using an apparatus comprising at least one processor; and at least one memory including computer program code.

In this example the machine-learning model has already been trained. The scanning process starts 404 by defining the maximum dose and the minimum reconstruction quality allowed. These values may be based on a database of known successful scans and current medical guidelines and legislation of allowed radiation dosage, for example. Also, for some medical conditions, the required reconstruction quality may be lower, so a smaller radiation dose will be enough. The minimum reconstruction quality may reflect the output quality error allowable between a reconstruction of the scans to be obtained and an ideal case (e.g. a reconstruction meeting a predetermined quality threshold).

The next step 406 is to take a low power scan (this can be e.g. one scan in a CT scan round or an ultra-low power 2D X-ray image, for example). The scan is then stored 408 to memory. All the scans taken so far in this imaging session are available 410 for later reconstruction 420. If the maximum dose is reached 412 following the latest scan 406, then the scanning process stops here. Then the final reconstruction takes place 418 using the scans taken 410, and a final reconstructed image 420 is obtained.

If the maximum dose is not yet met 412, then a pre-trained de-noising quality estimation model (a machine-learning error estimation model) is run on the scans taken so far 414. This model may be a machine-learning process, such as a deep neural network (convolutional neural network (CNN), recurrent neural network (RNN), fully connected (FC) neural network, or a combination thereof. The output from the quality estimation model, obtained during the scanning process (i.e. between scans) is an output quality error estimate which provides an estimate of the quality of the de-noising (that is, an estimate of the quality that a reconstructed output obtained from the scans taken so far would have). The quality estimate can be trained to be specific to the type of the scan or can be a generic de-noising quality estimate.

Steps 414 and 416 together may be considered to use a received output quality error estimate (a measure of the estimated de-noising or reconstruction quality), generated using a machine-learning error estimation model by comparing an output meeting a predetermined quality threshold with an output image reconstructed from a plurality of images. The generation of the output quality error estimate is discussed in more detail in relation to FIGS. 5-8. The received output quality error estimate from the machine-learning model is used to estimate if a second subsequent image is required 406, in addition to a first subsequent image 410 to obtain a cumulative output (e.g. reconstructed image) having an output quality error meeting a predetermined error threshold. That is, the machine-learning model is trained using known outputs/output images. Subsequent image scans may then be taken and a determination made in-between each subsequent scan (or each group of two or more subsequent scans) whether to continue capturing image scans or whether to stop capturing image scans (e.g. because the expected reconstruction from the acquired subsequent scans is of sufficient quality).

Following the estimation of reconstruction quality, if the de-noising confidence is good enough 416 (that is, the cumulative output from the subsequent scans is estimated by the machine learning model to have an output quality error meeting a predetermined error threshold), then the final reconstruction takes place 418 to obtain a final reconstructed image 420, and no further scans are taken. If the de-noising confidence is not good enough 416, then a further scan may be taken 406 provided the maximum dose has not been reached.

Once the de-noised reconstruction quality has been estimated 414, either it is decided to stop the scanning process, or continue it. In other words, the apparatus may, if the output quality error of the cumulative output meets or is below the predetermined error threshold (that is, the reconstructed output is expected to have high enough quality), provide an indication to stop recording images. If the output quality error exceeds the predetermined error threshold (that is, the reconstructed output is not expected to have high enough quality), the apparatus may provide an indication to record the second subsequent image and obtain an updated output quality error for the cumulative output including the second subsequent image.

The apparatus may be configured to estimate, in a time which is low enough to allow for the estimating to take place between successive subsequent images, if the second subsequent image is required. Because the apparatus considers an error in quality rather than a quality per se, the determination of whether a further scan is required or not can be performed quickly enough to take place between separate subsequent scans of a subject. The time to determine if a second subsequent image is required may be, for example, less than 1 second, less than 0.5 seconds, less than 0.2 seconds, and/or less than 0.1 seconds. It may be the time is short enough to allow for the estimation to take place between recording images of a human or animal subject (thus in a short enough time that the subject can remain stationary throughout recording all the subsequent scans).

Once the scanning process has been stopped, a more detailed final de-noised reconstruction may be created 418 from all of the collected scans 410. This final reconstruction 420 can be analytical, heuristic, or machine-learning based. Analytical reconstruction methods may be based on filtered backprojection (FBP), which is based on a one dimensional filter being performed on the projection data before back-projecting the data onto the image space. Heuristic methods may include iterative reconstruction methods (IR), which optimize an objective function iteratively. The objective function may contain a data fidelity term and an edge-preserving term for regularization. Some examples of IR methods may be slower to run than FBP methods. Machine learning methods include e.g. the aforementioned convolutional neural network (CNN) denoising method.

In other words, the apparatus may be configured to obtain a plurality of subsequent images including the first and second subsequent images; and after estimating that no further subsequent images are required to obtain a cumulative output having an output quality error meeting a predetermined error threshold, obtain the cumulative output by reconstructing an output image from the plurality of subsequent scans. In some examples, the apparatus may obtain the cumulative output by reconstructing an output diagnosis (estimate the final diagnosis) from the plurality of subsequent scans, and/or obtain the cumulative output by reconstructing an output segmentation (estimate the final segmentation) from the plurality of subsequent scans to indicate material types in the imaged subject. In some examples, the apparatus may obtain the cumulative output by reconstructing an output diagnosis (estimate the final diagnosis) and/or obtain the cumulative output by reconstructing an output segmentation (estimate the final segmentation) using a different method to the one that is used during the scanning process. In other words, a diagnosis and/or segmentation may be output in addition to an image. 2D, 3D, and/or 4D (3D plus the time dimension) outputs may be obtained using examples described herein.

The "reconstruction" may in some examples be a reconstructed image obtained from separate scan images, so that an estimated image error between an expected reconstructed image from the current data and an image reconstructed from previously obtained image data is obtained between scans, and a complete reconstructed image is not obtained between scans (but may be determined after scanning has finished). The reconstruction may in some examples be a diagnosis, so that an estimated error between an expected diagnosis from the current data and a diagnosis from previously obtained data is obtained between scans, and a complete diagnosis is not obtained between scans (but may be determined after scanning has finished). The reconstruction may in some examples be a segmentation (determination of material type regions, e.g. compact bone, spongy bone and bone marrow), so that an estimated error between an expected material type from the current data and a material type from previously obtained data is obtained between scans, and final determination of material type is not obtained between scans (but may be determined after scanning has finished).

In some examples, it may not be possible to obtain a high enough quality reconstructed output regardless of how many scans are taken (for example, if there is an error in the scanning equipment, or if the goal of the scanning is to identify a particular object such as a tumour or mass, which is too small to be identified in an image or segmentation). The apparatus may be configured to estimate that a cumulative output having an output quality error meeting a predetermined error threshold cannot be obtained by recording a second and further subsequent images; and provide an indication to stop recording images. The effect of this may be to reduce exposure of the subject to radiation, or at least reduce the extent to which the subject is unnecessarily imaged.

In some examples, the apparatus may comprise one or more of: a central processing unit, a field-programmable gate-array and an application-specific integrated circuit. By implementing the apparatus, at least partially, in a dedicated hardware circuit, the estimation may be performed more quickly than, for example, a software implementation on a general purpose computer/CPU. In some examples, a hardware accelerated (FPGA, ASIC) implementation of the quality estimation algorithm may be used to minimize the latency between the images/scan capture and the decision whether to stop or continue scanning.

Figure 5:
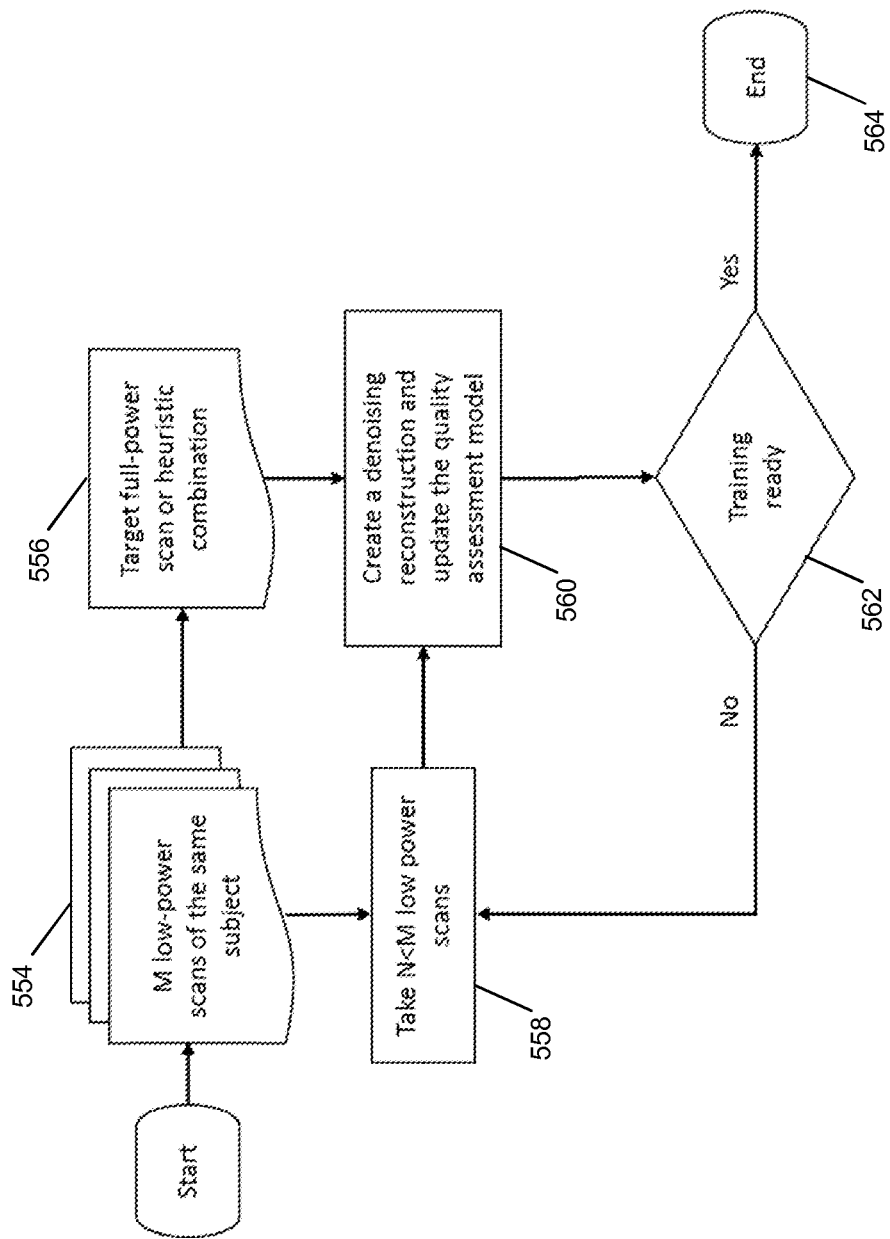
FIG. 5 illustrates an example general training process for a machine-learning model.

FIG. 5 illustrates an example training process to train the machine-learning model prior to recording scans of the subject of interest. The machine learning model may be termed a "quality assessment model", "error estimation model" or "machine learning error estimation model" as discussed above. In this example in FIG. 5 a single stochastic gradient descent step of the training is shown in the machine learning process. The training can stop when the quality assessment model has reached a good enough level using validation data (e.g. known/previously obtained data/scans), or when a certain predefined amount of training steps/iterations have been taken. This is one example of a possible training process, and other training processes may be used.

In this example, a single gradient descent step of the training process uses M low power scans of the same subject 554. M may be chosen so that the total dosage corresponds to a typical full power scan. Then the training process selects a random subset N (where N<M) of the low power scans 558 and updates a model 560 between the subset of the low power scans 558 and the expected reconstruction 556 (which may be obtained from full-power scan taken from the same subject). The model is updated 560 by creating a de-noised reconstruction from the subset of N scans. In addition, the quality assessment model may be updated using the difference between the estimated reconstruction from the M low power scans, and the target full-power scan, so that the model learns to estimate the expected quality of the reconstruction given the current scans. A sequential training of the machine-learning system is possible, for instance for a deep neural network, where any variant of stochastic gradient descent can be used.

In some examples, the machine learning model may continue being trained using a subsequently acquired scan or scans in conjunction with the data already used to trained the model. For example, in transfer learning, a pre-trained model can be re-trained with new data to improve performance or to perform a new task. In multi-task learning, multiple criteria (such as denoising and diagnosis) may be used simultaneously during training. Transfer learning and/or multi-task learning may be used to improve the training and/or the accuracy of the resulting model.

The trained quality assessment models can be generic (that is, trained using a body of data from various subjects, different scan parameters, varying doses, etc.) or can be task specific (that is, trained using a body of known data which corresponds to a subject having e.g. the same expected medical condition, or imaging the same body part, etc. as the subject to be imaged). The model may be generic or specific depending on the training data used in the training process. For the generic case, the machine learning system may estimate some quantity which can be obtained from the low power scans and compared to the full-power scans, such as mean squared error. In such examples, the output quality error estimate may be estimated using a machine-learning error estimation model to compare an output meeting a predetermined quality threshold with an output image reconstructed from a plurality of images, and the output quality error estimate may be provided for use in estimating if a second subsequent image is required, in addition to a first subsequent image, wherein each subsequent image need not necessarily be recorded using the same imaging parameters as the plurality of images used to reconstruct the output image used in obtaining the output quality error estimate, to obtain a cumulative output having an output quality error meeting a predetermined error threshold.

In task-specific examples, the output quality error estimate may be estimated using a machine-learning error estimation model to compare an output meeting a predetermined quality threshold with an output image reconstructed from a plurality of images recorded using particular (i.e. task-specific) imaging parameters, and the output quality error estimate may be provided for use in estimating if a second subsequent image is required, in addition to a first subsequent image, each subsequent image recorded using the same particular imaging parameters, to obtain a cumulative output having an output quality error meeting a predetermined error threshold.

The scans of the subject may also be aligned and unified as part of the scanning process. For instance, in deep learning, higher layers may be invariant to small changes in the input space, and that invariance may be used to create an invariant de-noising system. That is, for alignment, there may be many possible method which can be used, but a deep learning system can be able to learn to do the alignment itself.

In some examples, an additional model may be built and used which dynamically estimates the optimal amount of power required to obtain a good enough reconstructed output, based on previous scans in the current scanning process and the required quality and total power parameters.

Figure 6:
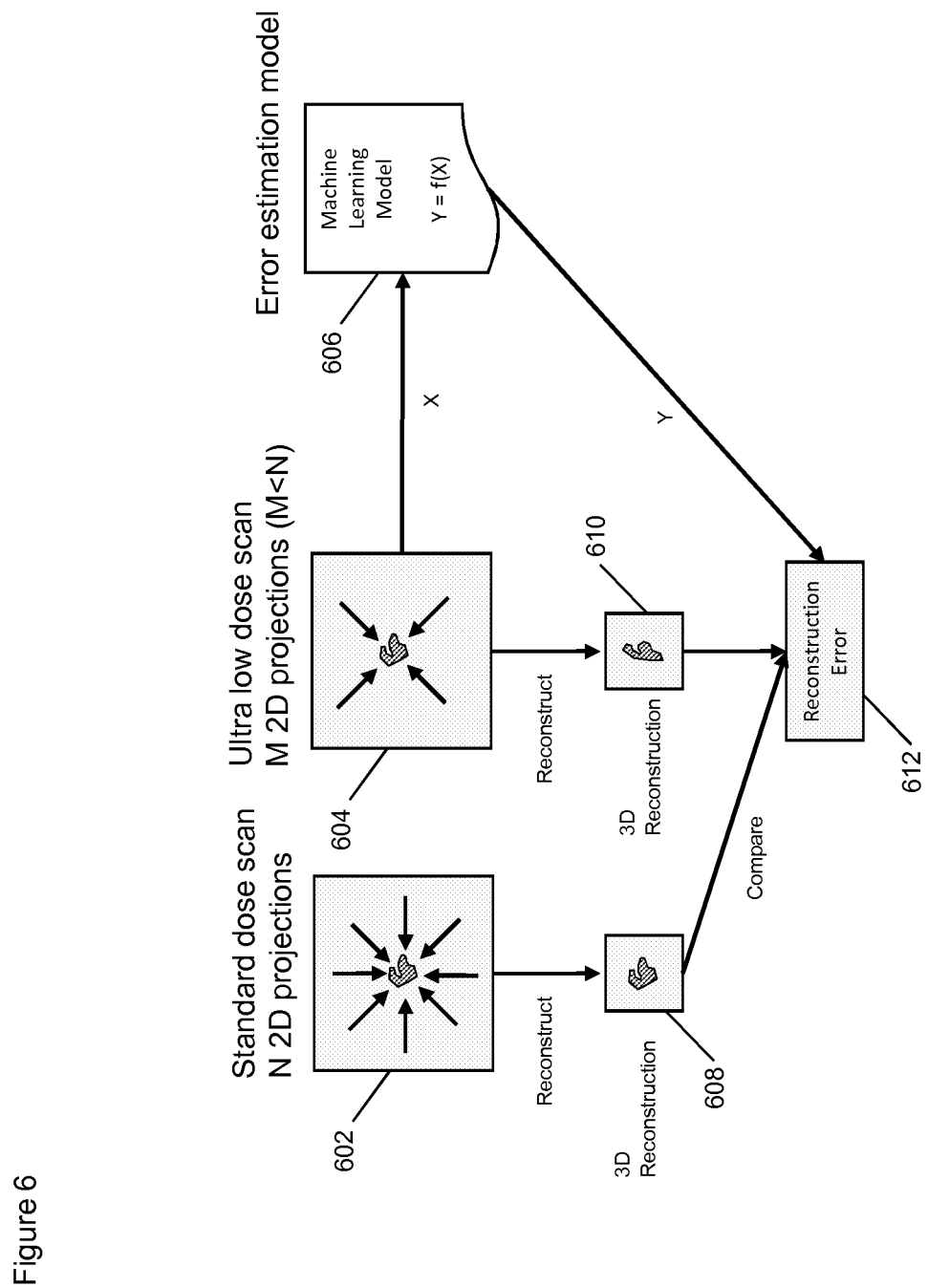
FIG. 6 illustrates an example general training process for a machine-learning model to provide an estimated reconstruction error.

FIG. 6 illustrates an example training process to train the machine-learning model prior to recording scans of the subject of interest. FIG. 6 relates to obtaining a reconstructed image of a subject. In FIG. 6, a series of N standard dose scans at different 2D angular projections 602 are used to reconstruct a 3D reconstruction of the imaged subject 608. The 3D reconstruction 608 may be considered to be an output meeting a predetermined quality threshold. Also, a series of M<N ultra-low dose scans at different 2D angular projections 604 are used to reconstruct a 3D reconstruction of the same imaged subject 610. An ultra-low dose may be below approximately 1 mSv, but this may vary depending on the target being imaged. The set of M ultra-low power scans may in some examples be a subset of the N standard power scans which are artificially altered to model an ultra-low dose image, or may be repeat scans taken at an ultra-low dose rather than at a standard dose, thus the same angular projection is used in both sets of data 602, 604. In some examples it need not be the case that the ultra-low dose scans 604 are taken at the same angular projection as a corresponding standard dose scan 602.

By comparing the 3D reconstruction from the standard dose scans 608 and the 3D reconstruction from the ultra-low dose scans 610, a reconstruction error 612 may be obtained. This reconstruction error indicates the difference in quality between a reconstruction obtained using standard I (high quality) dose scans and ultra-low (low quality) dose scans. The model only needs to learn to the estimate of the reconstruction error. The actual reconstruction, which can take a long time (too long to practically be performed in between taking scans of the subject) is done after the scans have all been taken.

The machine learning error estimation model 606 is provided with the ultra-low dose data 604 as X, and is provided with the corresponding reconstruction error 612 Y for that set of ultra-low dose data. Therefore the machine learning model can determine a function f such that Y=f(X), which links the reconstruction error Y 612 to the ultra-low dose data X 604. In other words, the machine learning model is trained that, for a particular ultra-low quality scan 604 X or series of such scans, the expected difference/error 612 between a 3D reconstruction 610 obtained using that ultra-low dose data 604, and an "ideal case" 608, is known. Thus, once trained, the machine learning model can be used to assess a subsequent ultra-low dose scan, and estimate what the error would be between a 3D reconstruction obtained using that subsequent scan or scans, and an ideal case. It can then indicate whether the latest subsequent scan is enough to obtain a sufficient quality output, and thus scanning may be stopped, or whether a further subsequent scan is required to improve/reduce the error to help meet a predetermined error threshold.

In this example, the output quality error estimate 612 is a reconstruction error indicating a difference between an image 608 reconstructed from a plurality of standard power classed images 602, the image meeting the predetermined quality threshold; and an image 610 reconstructed from a plurality of low power classed images 604. In this example, the predetermined error threshold to be met by the combined subsequent scans is an acceptable image noise threshold, and the output quality error of the cumulative output indicates that image noise of the cumulative output image would meet or be below the predetermined acceptable image noise threshold.

In some examples, the first subsequent image may be taken at a particular angular projection with respect to the subject, and the second subsequent image may be taken at a different particular angular projection with respect to the subject than the first subsequent image. For example, certain CT scans require different angular projections to be recorded to build up a 3D image of a subject. In other example, the first and second subsequent images may be taken at the same particular angular projection with respect to the subject. For example, if a 2D image is to be obtained, several low-dose X-ray shots may be taken at the same angular projection/from the same position, for later combination to produce a cumulative/combined image.

Figure 7:
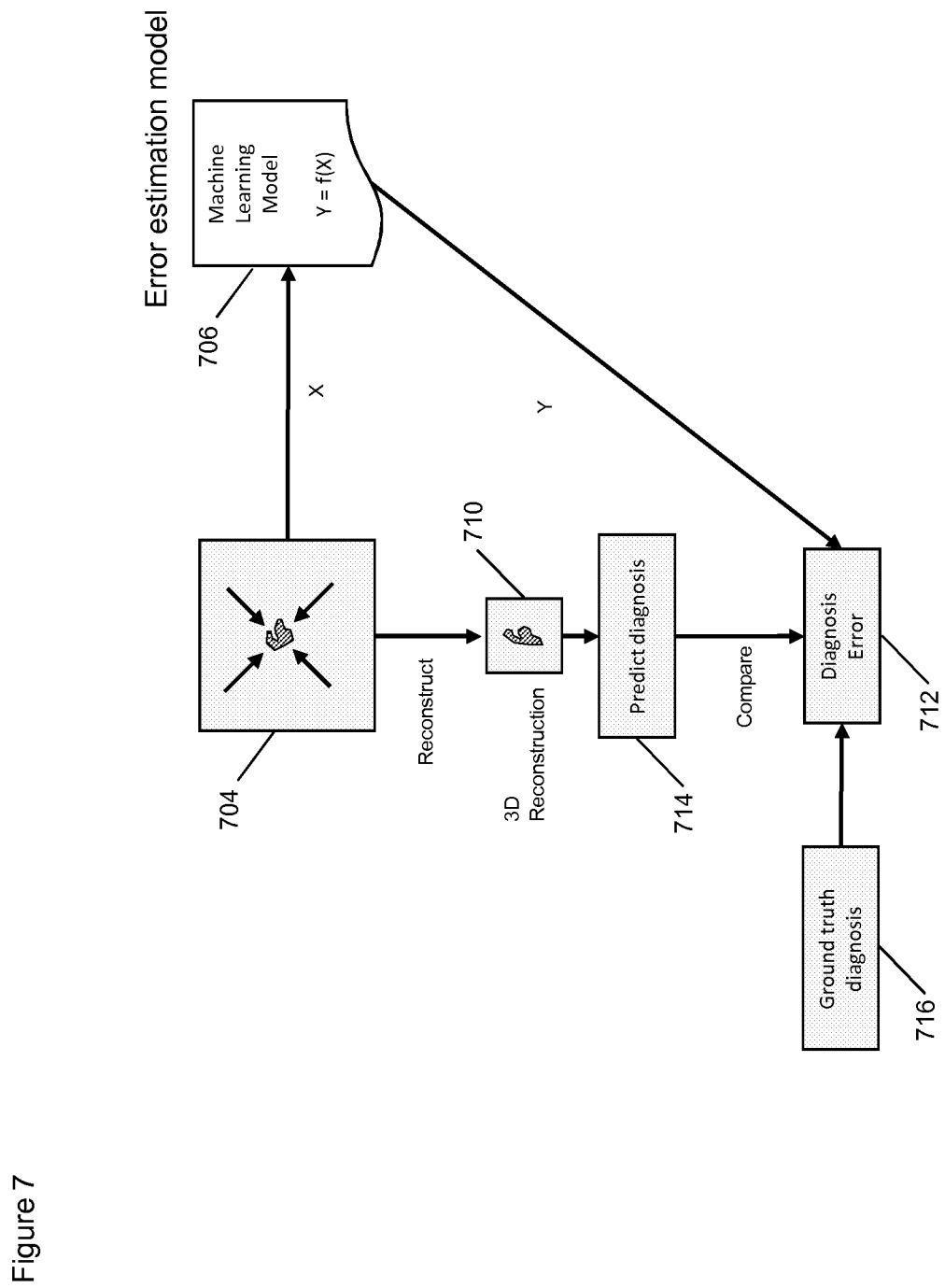
FIG. 7 illustrates an example general training process for a machine-learning model to provide an estimated diagnosis error.

FIG. 7 illustrates another example training process to train the machine-learning model prior to recording scans of the subject of interest. FIG. 7 relates to obtaining data from which a diagnosis of a subject may be obtained. In FIG. 7, a series of scans at different 2D angular projections 704 are used to reconstruct a 3D reconstruction of the same imaged subject 710, and from that 3D reconstruction, a diagnosis may be predicted 714.

The diagnosis 714 predicted from the scan data 704 is compared with a "ground truth" diagnosis 716, and the difference may be termed the diagnosis error 712, which is an output quality error estimate.

Similarly to the machine learning error estimation model of FIG. 6, the machine learning error estimation model 706 is provided with the scan data 704 as X, and is provided with the corresponding diagnosis error 712 Y for that set of data. Therefore the machine learning model can determine a function f such that Y=f(X), which links the diagnosis error Y 712 to the scan data X 704. In other words, the machine learning model is trained that, for a particular scan or set of scans 704 X, the expected difference/error 712 in confidence between a diagnosis 710 obtained using the scan data 704, and the "ground truth" diagnosis 716, is known. Thus, once trained, the machine learning model can be used to assess a subsequent scan, and estimate what the error in diagnosis would be between a 3D reconstruction obtained using that subsequent scan or scans, and an ideal case. It can then indicate whether the latest subsequent scan is enough to obtain a sufficient quality diagnosis output, and thus scanning may be stopped, or whether a further subsequent scan is required to improve/reduce the error to help meet a predetermined error threshold.

In this example, the output quality error estimate 712 is a diagnosis error indicating a difference between a diagnosis meeting the predetermined quality threshold 716, and a diagnosis 714 determined from an image 710 reconstructed from a plurality of low power classed images 704. In this example, the predetermined error threshold to be met by the combined subsequent scans is a diagnosis confidence threshold, and the output quality error estimate of the cumulative output indicates a confidence level that a diagnosis obtained from the cumulative output exceeds the predetermined diagnosis confidence threshold.

In another example (not illustrated), the output quality error estimate may be a segmentation error indicating a difference between an indication of material type meeting the predetermined quality threshold obtained from an image reconstructed from a plurality of standard power classed images; and an indication of material type determined from an image reconstructed from a plurality of low power classed images. In such an example, the predetermined error threshold to be met by the combined subsequent scans is a segmentation confidence threshold, and the output quality error of the cumulative output indicates a confidence level that a segmentation obtained from the cumulative output exceeds the predetermined segmentation confidence threshold.

Figure 8:
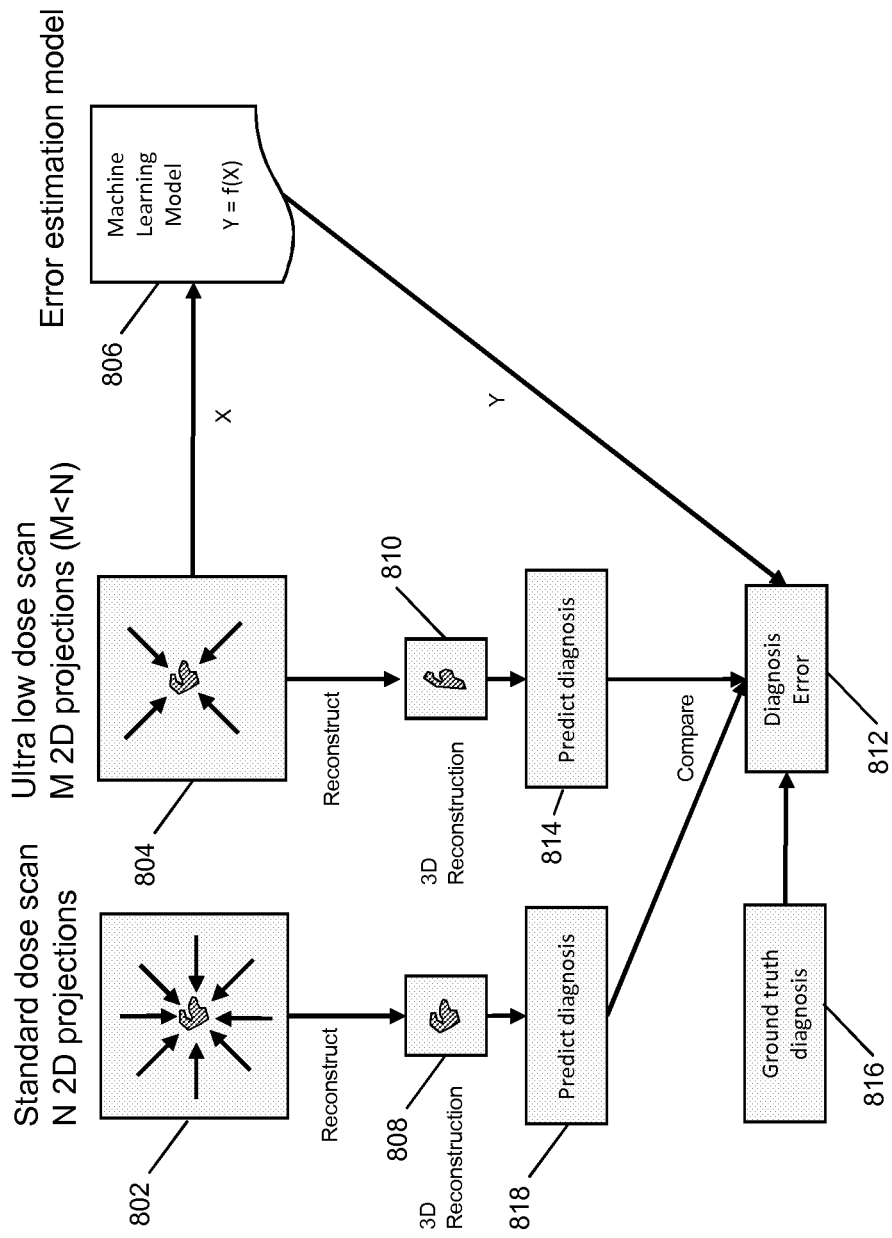
FIG. 8 illustrates another example general training process for a machine-learning model to provide an estimated diagnosis error.

FIG. 8 illustrates another example training process to train the machine-learning model prior to recording scans of the subject of interest. FIG. 8 relates to obtaining data from which a diagnosis of a subject may be obtained. In FIG. 8, a series of low dose scans at different 2D angular projections 804 are used to reconstruct a 3D reconstruction of the same imaged subject 810, and from that 3D reconstruction 810, a diagnosis may be predicted 814.

The diagnosis 814 predicted from the low dose scan data 804 is compared with both a "ground truth" diagnosis 816 (as in FIG. 7), and a predicted diagnosis 818 obtained from a 3D reconstruction 808 reconstructed from a series of standard dose scans 802. The difference between the diagnosis 814 obtained from the low dose 3D reconstruction 810 and the ground truth diagnosis 816 and diagnosis 818 obtained from the standard dose 3D reconstruction 808 may be termed the diagnosis error 812, which is an output quality error estimate.

Similarly to the machine learning error estimation models of FIGS. 6 and 7, the machine learning error estimation model 806 is provided with the low dose scan data 804 as X, and is provided with the corresponding diagnosis error 812 Y for that set of data. Therefore the machine learning model can determine a function f such that Y=f(X), which links the diagnosis error Y 812 to the low dose scan data X 804. In other words, the machine learning model is trained that, for a particular scan or set of low dose scans 804 X, the expected difference/error 812 in confidence between a diagnosis 810 obtained using the low dose scan data 804, and the "ground truth" diagnosis 816 or diagnosis 818 obtained from a 3D reconstruction 818 of standard dose scan data 802, is known. Thus, once trained, the machine learning model can be used to assess a subsequent low dose scan, and estimate what the error in diagnosis would be between a 3D reconstruction obtained using that subsequent low dose scan or scans, and an ideal case.

Thus, from FIGS. 6-8, an apparatus may be configured to generate an output quality error estimate 612, 712, 812 using a machine-learning error estimation model 606, 706, 806 to compare an output 608, 716, 816, 818 meeting a predetermined quality threshold with an output image 610, 710, 810 reconstructed from a plurality of images 604, 704, 804, and provide the output quality error estimate 612, 712, 812 for use in estimating if a second subsequent image is required, in addition to a first subsequent image to obtain a cumulative output having an output quality error meeting a predetermined error threshold.

Examples disclosed herein may provide for a reduction or minimisation in the harmful radiation dosage received by the patient due to being scanned with X-rays, while providing the required quality level of the reconstruction. In some cases the scanning process may be sped up using examples disclosed herein due to, for example, identification that no further scans are required which may not otherwise be known until all scans in a planned series (e.g. up to a maximum radiation dosage) have been taken.

In some examples, algorithms for aligning the different scans may be utilized before the quality assessment and reconstruction algorithms are used. In other words, it may be possible to pre-process the data in various ways before feeding it in to the machine learning models. For instance, when scanning an organ with motion, such as the lungs or heart, there may be existing methods which can be used to align the images taken at different times. Such alignment pre-processing may be used in combination with quality assessment and reconstruction algorithms, provided the alignment pre-processing algorithms may be run quickly enough.

FIG. 9 shows the main steps of a method 900 of training a machine learning error estimation model, namely generating an output quality error estimate using a machine-learning error estimation model to compare an output meeting a predetermined quality threshold with an output image reconstructed from a plurality of images 902, and providing the output quality error estimate for use in estimating if a second subsequent image is required, in addition to a first subsequent image to obtain a cumulative output having an output quality error meeting a predetermined error threshold 904.

FIG. 10 shows the method 1000 of using a trained machine learning error estimation model, namely using an output quality error estimate, generated using a machine-learning error estimation model by comparing an output meeting a predetermined quality threshold with an output image reconstructed from a plurality of images, to estimate if a second subsequent image is required, in addition to a first subsequent image to obtain a cumulative output having an output quality error meeting a predetermined error threshold 1002.

FIG. 11 illustrates schematically a computer/processor readable medium 1100 providing a computer program according to one example. The computer program may comprise computer code configured to perform, control or enable one or more of the methods of FIGS. 9 and 10. In this example, the computer/processor readable medium 1000 is a disc such as a digital versatile disc (DVD) or a compact disc (CD). In other examples, the computer/processor readable medium 1000 may be any medium that has been programmed in such a way as to carry out an inventive function. The computer/processor readable medium 1000 may be a removable memory device such as a memory stick or memory card (SD, mini SD, micro SD or nano SD card).

The term "subject" is used to describe the item being imaged, such as an object, chemical or biological sample, or body (e.g. a human or animal body or body part/portion, living or dead).

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some examples, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such examples can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some examples one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed examples may consist of any such individual feature or combination of features. In view of the foregoing description it will be evident to a person skilled in the art that various modifications may be made within the scope of the disclosure.

While there have been shown and described and pointed out fundamental novel features as applied to different examples thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or example may be incorporated in any other disclosed or described or suggested form or example as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising:
   at least one processor; and
   at least one memory including computer program code,
   the at least one memory and the computer program code configured to, with the at least one processor, cause the apparatus to:
   generate an output quality error estimate using a machine-learning error estimation model to compare a first output meeting a predetermined quality threshold, the first output being based on a first reconstructed image obtained from a first plurality of images, with a second output image reconstructed from a second plurality of images, and
   provide the output quality error estimate for use in estimating if a second subsequent image is required, in addition to a first subsequent image to obtain a cumulative output having an output quality error meeting a predetermined error threshold.

2. The apparatus of claim 1, wherein:
   the second output image used to generate the output quality error estimate is an image reconstructed from the second plurality of images recorded using particular imaging parameters; and
   the first and second subsequent images are recorded using the particular imaging parameters.

3. The apparatus of claim 1, wherein the output quality error estimate is one or more of:
   a reconstruction error indicating a difference between:
      the first reconstructed image, wherein the first reconstructed image is reconstructed from the first plurality of images comprising a plurality of standard power classed images; and
      the second output image reconstructed from the second plurality of images comprising a plurality of low power classed images;

a diagnosis error indicating a difference between:
  a first diagnosis determined from the first reconstructed image; and
  a second diagnosis determined from the second output image reconstructed from the plurality of low power classed images; and
a segmentation error indicating a difference between:
  a first indication of a material type meeting the predetermined quality threshold obtained from the first reconstructed image reconstructed from the plurality of standard power classed images; and
  a second indication of a material type determined from the second output image reconstructed from the plurality of low power classed images.

4. The apparatus of claim 3, wherein the predetermined error threshold is one of:
  an acceptable image noise threshold, and the output quality error of the cumulative output indicates that image noise of the cumulative output meets or is below the predetermined acceptable image noise threshold, wherein the cumulative output is a cumulative output image obtained by reconstructing the first and/or second subsequent images;
  a diagnosis confidence threshold, and the output quality error of the cumulative output indicates a confidence level that the cumulative diagnosis exceeds the predetermined diagnosis confidence threshold, wherein the cumulative output is obtained by reconstructing an output diagnosis from the first and/or second subsequent images; or
  a segmentation confidence threshold, and the output quality error of the cumulative output indicates a confidence level that the cumulative segmentation exceeds the predetermined segmentation confidence threshold, wherein the cumulative output is obtained by reconstructing an output segmentation from the first and/or second subsequent images.

5. The apparatus of claim 4, wherein the apparatus is configured to:
  receive data representing a plurality of subsequent images including the first and second subsequent images; and
  after estimating that no further subsequent images are required to obtain a cumulative output having an output quality error meeting a predetermined error threshold, obtain the cumulative output by reconstructing the cumulative output image from the plurality of subsequent images.

6. The apparatus of claim 1, wherein the apparatus is configured to:
  if the output quality error of the cumulative output meets or is below the predetermined error threshold, provide an indication to stop recording images; and
  if the output quality error exceeds the predetermined error threshold, provide an indication to record the second subsequent image.

7. The apparatus of claim 1, wherein the apparatus is further configured to, if the output quality error of the cumulative output exceeds the predetermined error threshold, obtain an updated output quality error for the cumulative output including the second subsequent image.

8. The apparatus of claim 1, wherein the apparatus is configured to estimate if the second subsequent image is required between acquisition of successive subsequent images.

9. The apparatus of claim 1, wherein the apparatus is configured to:
  estimate that a cumulative output having an output quality error meeting a predetermined error threshold cannot be obtained by recording a second and further subsequent images; and
  provide an indication to stop recording images.

10. The apparatus of claim 1, wherein the first and second subsequent images are:
  X-ray images, Computer Tomography scan images, Magnetic Resonance Imaging images, functional Magnetic Resonance Imaging images, fusion imaging, positron emission tomography images, single photon emission tomography, Magnetoencephalography (MEG) images or ultrasound images.

11. The apparatus of claim 1, wherein the apparatus is configured to estimate if a second subsequent image is required following one or more of: a single first subsequent image, and a plurality of first subsequent images.

12. An apparatus comprising:
  at least one processor; and
  at least one memory including computer program code,
  the at least one memory and the computer program code configured to, with the at least one processor, cause the apparatus to:
  use a received output quality error estimate, generated using a machine-learning error estimation model by comparing a first output meeting a predetermined quality threshold, the first output being based on a first reconstructed image obtained from a first plurality of images, with a second output image reconstructed from a second plurality of images, to estimate if a second subsequent image is required, in addition to a first subsequent image to obtain a cumulative output having an output quality error meeting a predetermined error threshold.

13. A computer-implemented method comprising:
  generating an output quality error estimate using a machine-learning error estimation model to compare a first output meeting a predetermined quality threshold, the first output being based on a first reconstructed image obtained from a first plurality of images, with a second output image reconstructed from a second plurality of images, and
  providing the output quality error estimate for use in estimating if a second subsequent image is required, in addition to a first subsequent image to obtain a cumulative output having an output quality error meeting a predetermined error threshold.

14. A computer program product comprising a non-transitory computer-readable medium having computer readable code stored thereon, the computer readable code, when executed by at least one processor, causing an apparatus to perform the method of claim 13.

15. A computer-implemented method comprising:
  using an output quality error estimate, generated using a machine-learning error estimation model by comparing a first output meeting a predetermined quality threshold, the first output being based on a first reconstructed image obtained from a first plurality of images, with a second output image reconstructed from a second plurality of images, to estimate if a second subsequent image is required, in addition to a first subsequent image to obtain a cumulative output having an output quality error meeting a predetermined error threshold.

16. A computer program product comprising a non-transitory computer-readable medium having computer readable code stored thereon, the computer readable code, when executed by at least one processor, causing an apparatus to perform the method of claim 15.

\* \* \* \* \*